US010344008B2

(12) United States Patent
Wolf et al.

(10) Patent No.: US 10,344,008 B2
(45) Date of Patent: Jul. 9, 2019

(54) PROCESS FOR THE PREPARATION OF TERPINOLENE EPOXIDE

(71) Applicant: BASF AGRO B.V., Arnhem (NL)

(72) Inventors: Bernd Wolf, Niederkirchen (DE); Michael Rack, Eppelheim (DE); Stefan Benson, Bensheim (DE); Helmut Kraus, Wissembourg (FR); Roland Goetz, Neulussheim (DE); Sukunath Narayanan, Mumbai (IN); Chidambaram Rishinaradamangalam, Hosur (IN)

(73) Assignee: BASF AGRO B.V., Arnhem (NL)

( * ) Notice: Subject to any disclaimer, the term of this patent is extended or adjusted under 35 U.S.C. 154(b) by 0 days.

(21) Appl. No.: 15/571,627

(22) PCT Filed: Apr. 28, 2016

(86) PCT No.: PCT/EP2016/059464
§ 371 (c)(1),
(2) Date: Nov. 3, 2017

(87) PCT Pub. No.: WO2016/180642
PCT Pub. Date: Nov. 17, 2016

(65) Prior Publication Data
US 2018/0141924 A1 May 24, 2018

(30) Foreign Application Priority Data

May 8, 2015 (IN) .......................... 1292/DEL/2015
Jun. 30, 2015 (EP) ....................................... 15174602

(51) Int. Cl.
C07D 301/12 (2006.01)
C07C 29/17 (2006.01)
C07C 29/56 (2006.01)
C07C 35/18 (2006.01)
C07D 303/04 (2006.01)
C07D 493/08 (2006.01)

(52) U.S. Cl.
CPC ............ *C07D 301/12* (2013.01); *C07C 29/17* (2013.01); *C07C 29/56* (2013.01); *C07C 35/18* (2013.01); *C07D 303/04* (2013.01); *C07D 493/08* (2013.01)

(58) Field of Classification Search
CPC .. C07D 301/12; C07D 493/08; C07D 303/04; C07C 29/17; C07C 29/56; C07C 35/18
USPC ......................................................... 549/531
See application file for complete search history.

(56) References Cited

U.S. PATENT DOCUMENTS

| 3,676,504 A * | 7/1972 | Leffingwell ............. C07C 35/18 568/825 |
| 4,257,948 A * | 3/1981 | Costerousse ........... C07J 71/001 540/25 |
| 4,487,945 A | 12/1984 | Payne |
| 4,542,244 A | 9/1985 | Payne et al. |
| 4,898,954 A | 2/1990 | Mohrmann et al. |
| 4,945,100 A | 7/1990 | Nyfeler et al. |
| 4,992,458 A | 2/1991 | Riebli et al. |
| 5,143,932 A | 9/1992 | Jautelat et al. |
| 2017/0305849 A1 | 10/2017 | Schäfer et al. |

FOREIGN PATENT DOCUMENTS

| CA | 1171866 A | 7/1984 |
| CA | 1209152 A | 8/1986 |
| CN | 1467029 A | 1/2004 |
| CN | 101602770 A | 12/2009 |
| DE | 3042302 A1 | 8/1981 |
| DE | 3315681 A1 | 10/1984 |
| DE | 3733755 A1 | 4/1989 |
| DE | 4003180 A1 | 8/1991 |
| EP | 0081893 B1 | 3/1987 |
| EP | 0113640 B1 | 5/1990 |
| EP | 0275955 B1 | 7/1990 |
| EP | 0126430 B1 | 8/1991 |
| EP | 0298020 B1 | 6/1992 |
| EP | 0735142 B1 | 10/2001 |
| GB | 1307053 A | 2/1973 |
| JP | H0248541 A | 2/1990 |
| WO | 2002085891 A1 | 10/2002 |
| WO | 2006128126 A1 | 11/2006 |
| WO | 2013007767 A1 | 1/2013 |
| WO | 2013010862 A1 | 1/2013 |
| WO | 2013066360 A1 | 5/2013 |
| WO | 2013124791 A1 | 8/2013 |
| WO | 2013189910 A1 | 12/2013 |
| WO | 2014012811 A1 | 1/2014 |
| WO | 2014026845 A1 | 2/2014 |
| WO | 2014026893 A1 | 2/2014 |
| WO | 2014026928 A1 | 2/2014 |
| WO | 2014060449 A1 | 4/2014 |
| WO | 2014108286 A1 | 7/2014 |
| WO | 2014111398 A1 | 7/2014 |

(Continued)

OTHER PUBLICATIONS

Vliet et al, Hexafluoracetone in Hexafluoro-2-propanol: A highly Active Medium for Epoxidation with Aqueous Hydrogen Peroxide, Synlett, No. 8, p. 1305-1307. (Year: 2001).*
Aldrich, "Handbook of Fine Chemicals" 1998-1999, p. 367 and 1645-1646.
Brandes and Jacobsen, "Synthesis of Enantiopure 3-chlorostyrene Oxide via an Asymmetric Epoxidation-Hydrolytic Kinetic Resolution Sequence," Tetrahedron:Asymmetry, vol. 8, No. 23, (1997), pp. 3927-3933.
Forrester et al., "Generation of Trimethylsulfonium Cation from Dimethyl Sulfoxide and Dimethyl Sulfate: Implications for the Synthesis of Epoxides from Aldehydes and Ketones," J. Chem. Soc. Perkin Trans. (1995), pp. 2289-2291.
Kuzenkov, "Synthesis of Substituted 2-azolyl-1-pyridylethan-1-ols," Chemistry of Heterocyclic Compounds, vol. 39, No. 11, (2003), pp. 1492-1495.

(Continued)

*Primary Examiner* — Taylor V Oh
(74) *Attorney, Agent, or Firm* — Brinks Gilson & Lione

(57) ABSTRACT

The present invention relates to a process for the preparation of terpinolene epoxide by epoxidation of terpinolene.

19 Claims, No Drawings

(56) References Cited

FOREIGN PATENT DOCUMENTS

| | | |
|---|---|---|
| WO | 2014135392 A1 | 9/2014 |
| WO | 2014155214 A1 | 10/2014 |
| WO | 2014184014 A1 | 11/2014 |
| WO | 2014184015 A1 | 11/2014 |
| WO | 2014184016 A1 | 11/2014 |
| WO | 2014184017 A1 | 11/2014 |
| WO | 2014184019 A1 | 11/2014 |
| WO | 2014184073 A1 | 11/2014 |
| WO | 2014184074 A1 | 11/2014 |
| WO | 2014187705 A1 | 11/2014 |
| WO | 2014202589 A1 | 12/2014 |
| WO | 2015003858 A1 | 1/2015 |
| WO | 2015007564 A1 | 1/2015 |
| WO | 2015011119 A2 | 1/2015 |
| WO | 2015011120 A2 | 1/2015 |
| WO | 2015022634 A2 | 2/2015 |
| WO | 2015049160 A1 | 4/2015 |
| WO | 2015049360 A1 | 4/2015 |
| WO | 2015052152 A1 | 4/2015 |
| WO | 2015052153 A1 | 4/2015 |
| WO | 2015052173 A1 | 4/2015 |
| WO | 2015052178 A1 | 4/2015 |
| WO | 2015055447 A1 | 4/2015 |
| WO | 2015067494 A1 | 5/2015 |
| WO | 2015075087 A1 | 5/2015 |
| WO | 2015082415 A1 | 6/2015 |
| WO | 2015082422 A2 | 6/2015 |
| WO | 2015086596 A1 | 6/2015 |
| WO | 2015086698 A1 | 6/2015 |
| WO | 2015091045 A1 | 6/2015 |
| WO | 2015124651 A1 | 8/2015 |
| WO | 2015155236 A1 | 10/2015 |
| WO | 2015158518 A1 | 10/2015 |
| WO | 2015158565 A1 | 10/2015 |
| WO | 2015169883 A1 | 11/2015 |
| WO | 2016001025 A1 | 1/2016 |
| WO | 2016005211 A1 | 1/2016 |
| WO | 2016016369 A1 | 2/2016 |
| WO | 2016037785 A1 | 3/2016 |
| WO | 2016055404 A1 | 4/2016 |
| WO | 2016062814 A1 | 4/2016 |
| WO | 2016071243 A1 | 5/2016 |
| WO | 2016180614 A1 | 11/2016 |
| WO | 2016180642 A1 | 11/2016 |
| WO | 2016180833 A1 | 11/2016 |
| WO | 2016202807 A1 | 12/2016 |
| WO | 2017009054 A1 | 1/2017 |
| WO | 2017009056 A1 | 1/2017 |
| WO | 2017009060 A1 | 1/2017 |
| WO | 2017009061 A1 | 1/2017 |
| WO | 2017009088 A1 | 1/2017 |
| WO | 2017009089 A1 | 1/2017 |
| WO | 2017009090 A1 | 1/2017 |
| WO | 2017009092 A1 | 1/2017 |
| WO | 2017009095 A1 | 1/2017 |
| WO | 2017009124 A1 | 1/2017 |
| WO | 2017009134 A1 | 1/2017 |
| WO | 2017009137 A1 | 1/2017 |
| WO | 2017009138 A1 | 1/2017 |
| WO | 2017009139 A1 | 1/2017 |
| WO | 2017009140 A1 | 1/2017 |
| WO | 2017009142 A1 | 1/2017 |
| WO | 2017009143 A1 | 1/2017 |
| WO | 2017009144 A1 | 1/2017 |
| WO | 2017009145 A1 | 1/2017 |
| WO | 2017009146 A1 | 1/2017 |
| WO | 2017009147 A1 | 1/2017 |
| WO | 2017009148 A1 | 1/2017 |
| WO | 2017012938 A1 | 1/2017 |
| WO | 2017102905 A1 | 6/2017 |
| WO | 2017133942 A1 | 8/2017 |
| WO | 2017144336 A1 | 8/2017 |
| WO | 2017144337 A1 | 8/2017 |

OTHER PUBLICATIONS

Afon'Kin et al., "Synthesis of Some Electron-Rich Aryl(hetaryl)oxiranes under Phase-Transfer and Homogeneous Conditions," Russian Journal of Organic Chemistry, vol. 44, No. 12, (2008), pp. 1776-1779.

Corey and Chaykovsky, "Dimethyloxosulfonium Methylide ((CH3)2SOCH2) and Dimethylsulfonium Methylide ((CH3)2SCH2). Formation and Application to Organic Synthesis," Journal of American Chemical Society, vol. 87, No. 6, (1965), pp. 1353-1364.

Mosset and Grée, "Trimethylsulfonium Methylsulfate, a Simple and Efficient Epoxidizing Agent," Synthetic Communications, vol. 15, No. 8, (1985), pp. 749-757.

Yu et al., "Synthesis and Fungicidal Evaluation of 2-Arylphenyl Ether-3-(1H-1,2,4-triazol-l-yl)propan-2-ol Derivatives," J. Agric. Food Chem., vol. 57, No. 11, (2009), pp. 4854-4860.

Uguina et al., "Alumina as Heterogeneous Catalyst for the Regioselective Epoxidation of Terpenic Diolefins with Hydrogen Peroxide," Journal of Molecular Catalysis A: Chemical, 2006, vol. 256, pp. 208-215.

Van Vliet et al., "Hexafluoroacetone in Hexafluoro-2-propanol: A Highly Active Medium for Epoxidation with Aqueous Hydrogen Peroxide," Synlett, No. 8, (2001), pp. 1305-1307.

Gurudutt et al., "Acid-Catalysed Rearrangement of Terpinolene Oxide," Indian Journal of Chemistry, Section B, Council of Scientific and Industrial Research, vol. 24B, (1985), pp. 820-823.

The Pesticide Manual, 14th Ed., C.D.S. Tomlin, British Crop Production Council, Entry 157, (2006), pp. 195-196.

* cited by examiner

PROCESS FOR THE PREPARATION OF TERPINOLENE EPOXIDE

CROSS-REFERENCE TO RELATED APPLICATIONS

This application is a National Stage application of International Application No. PCT/EP2016/059464, filed Apr. 28, 2016. This application also claims priority under 35 U.S.C. § 119 to European Patent Application No. 15174602.1, filed Jun. 30, 2015 and Indian Patent Application No. 1292/DEL/2015, filed May 8, 2015.

This invention relates to a process for the preparation of terpinolene epoxide (I) by epoxidation of terpinolene

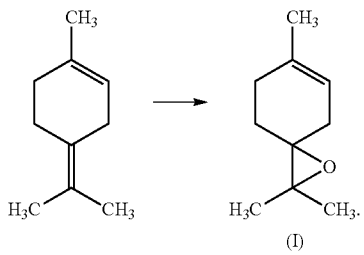

(I)

Terpinolene epoxide is a valuable intermediate in the synthesis of terpinene-4-ol—an unsaturated tertiary terpene alcohol that occurs naturally in a number of essential oils. Terpinene-4-ol finds use as a component in synthetic essential oils which are compounded for use as flavors or perfumes. Because of high costs and uncertainty of supply of the natural product, synthetic routes to terpinene-4-ol have been developed, e.g. via epoxidation route starting from epoxidation of terpinolene. Nevertheless, there is still room for improvement with regard to the epoxidation step.

U.S. Pat. No. 3,676,504 describes a process for the preparation of terpinolene epoxide by epoxidation of terpinolene using organic peroxy acids, such as peracetic, perpropionic or m-chloroperbenzoic acid as oxidizing agents. The solvent used is methylene chloride. The reactions with peroxy acids, however, are often very exothermic and require a proper cooling and dilution for preventing explosions. This leads to a low space-time yield and makes such reactions not very suitable for an industrial scale preparation.

U.S. Pat. No. 4,257,948 describes a process for epoxidation of unsaturated organic compounds having at least one double bond using hexachloroacetone and hydrogen peroxide. The compound to be epoxidized may be acyclic, cyclic or polycyclic. Terpenic derivatives are mentioned as an example of monocyclic compounds. The reaction is effected in a chlorinated organic solvent, such as methylene chloride or chloroform, and requires cooling prior to addition of hydrogen peroxide. In industrial processes, however, it is desired to avoid cooling in order to save resources and energy.

It was accordingly an object of the present invention to provide an industrially simple process for the preparation of terpinolene epoxide in good yields. In addition, the process should be environmentally friendly in order to reduce unfavorable environmental effects.

Surprisingly we have found that these and further objects are, in part or in whole, achieved by the process of the present invention wherein terpinolene is reacted with an oxidizing agent comprising hydrogen peroxide in the presence of a halogenated ketone selected from halogenated di-($C_1$-$C_6$)-alkyl ketones and halogenated ($C_1$-$C_6$)-alkyl phenyl ketones and the reaction is carried out in the absence of a halogenated organic solvent.

Accordingly, said process for the preparation of terpinolene epoxide is a subject matter of the present invention.

The process according to the present invention entails a series of advantages and overcomes drawbacks of the prior art processes. It can be carried out at a room temperature and does not require sophisticated cooling equipment. The reaction time is short. The process does not utilize chlorinated organic solvents that are generally harmful to human and environmental health and require special safety measures to be taken. Any and all of these advantages this saves resources and energy. Terpinolene epoxide is obtained in good yields and the process provides a very good chemoselective epoxidation of the exocyclic double bond. Undesired side reactions leading to unwanted by-products are minimized. Sometimes, the product can be employed in the next reaction step without purification. These advantages make the process industrially simple and environmentally friendly.

Further embodiments of the invention are evident from the claims, the description and the examples. It is to be understood that the single features of the subject matter of the invention described herein can be applied not only in the combination given in each particular case but also in other combinations, without leaving the scope of the invention.

The epoxidation of terpinolene according to the present invention is carried out in the presence of hydrogen peroxide and a halogenated ketone as a catalyst.

The term "halogenated" as used herein refers to fluorinated, chlorinated, brominated or iodinated radical. Halogenated radical can be partially or fully halogenated, i.e. 1, 2, 3, 4 or 5 or all of the hydrogen atoms of a given radical can be replaced by a halogen atom. A partially or fully halogenated radical is also termed "halo-radical". For example, partially or fully halogenated alkyl is termed as "haloalkyl".

Preferably, the halogenated ketone of the present invention is selected from fluorinated or chlorinated ketones, more preferably from chlorinated ketones.

The halogenated ketone of the present invention is selected from halogenated di-($C_1$-$C_6$)-alkyl ketones and halogenated ($C_1$-$C_6$)-alkyl phenyl ketones, preferably from halogenated di-($C_1$-$C_4$)-alkyl ketones and halogenated ($C_1$-$C_4$)-alkyl phenyl ketones.

In another preferred embodiment of the present invention, the halogenated ketone is selected from halogenated di-($C_1$-$C_6$)-alkyl ketones, preferably from halogenated di-($C_1$-$C_4$)-alkyl ketones.

Alkyl chains of the alkyl radicals can be straight or branched. The prefix $C_n$-$C_m$ denotes in each case the possible number of carbon atoms in the group.

Examples of such radicals are:

$C_1$-$C_4$-alkyl: for example methyl, ethyl, n-propyl, isopropyl, n-butyl, 2-butyl (sec-butyl), iso-butyl, tert-butyl;

$C_1$-$C_6$-alkyl: $C_1$-$C_4$-alkyl as mentioned above, and also, for example, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, 2-ethylpropyl, n-hexyl, 1-methylpentyl, 2-methyl pentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl; preferably methyl, ethyl, n-propyl, i-propyl, n-butyl and the like;

$C_1$-$C_4$-haloalkyl: $C_1$-$C_4$-alkyl as mentioned above which are partially or fully substituted by fluorine, chlorine, bromine and/or iodine, for example, chloromethyl, di-chloromethyl, trichloromethyl, fluoromethyl, difluoromethyl, trifluoromethyl, chloro-fluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3 trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl, 1-trifluoromethyl-1,2,2,2-tetrafluoroethyl and the like;

$C_1$-$C_6$-haloalkyl: $C_1$-$C_4$-haloalkyl and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl, dodecafluorohexyl and the like;

Preferably, the halogenated ketone of the present invention is selected from hexafluoroacetone, hexachloroacetone, perfluoromethylisopropyl ketone, perfluoromethylethyl ketone, 2,2,2-trifluoroacetophenone, 2,2,2-trichloroacetophenone and any mixture thereof.

Even more preferably, the halogenated ketone of the present invention is selected from hexafluoroacetone, hexachloroacetone and a mixture thereof. Preferably, the halogenated ketone of the present invention is hexachloroacetone.

Equally preferably, the halogenated ketone of the present invention is selected from perfluoromethylisopropyl ketone, perfluoromethylethyl ketone and a mixture thereof. Preferably, the halogenated ketone of the present invention is perfluoromethylisopropyl ketone.

Yet equally preferably, the halogenated ketone of the present invention is selected from 2,2,2-trifluoroacetophenone, 2,2,2-trichloroacetophenone and a mixture thereof. Preferably, the halogenated ketone of the present invention is 2,2,2-trichloroacetophenone.

In another embodiment, the halogenated ketone is selected from hexachloroacetone, perfluoromethyl isopropyl ketone, 2,2,2-trichloroacetophenone and any mixture thereof.

The starting materials according to the present invention are known compounds that are commercially available or can be prepared in a known manner.

In one embodiment, the epoxidation reaction according to the present invention is carried out in the absence of a halogenated organic solvent.

In another embodiment, the reaction is carried out in the absence of a halogenated organic solvent except halogenated di-($C_1$-$C_6$)-alkyl ketones and halogenated ($C_1$-$C_6$)-alkyl phenyl ketones (preferably halogenated di-($C_1$-$C_4$)-alkyl ketones and halogenated ($C_1$-$C_4$)-alkyl phenyl ketones).

In another embodiment, the reaction is carried out in the absence of a halogenated organic solvent except halogenated di-($C_1$-$C_6$)-alkyl ketones (preferably halogenated di-($C_1$-$C_4$)-alkyl ketones).

In another embodiment, the reaction is carried out in the absence of a halogenated organic solvent except hexafluoroacetone, hexachloroacetone, perfluoromethylisopropyl ketone, perfluoromethylethyl ketone, 2,2,2-trifluoroacetophenone, 2,2,2-trichloroacetophenone and any mixture thereof.

In another embodiment, the reaction is carried out in the absence of a halogenated organic solvent except hexafluoroacetone, hexachloroacetone and a mixture thereof (preferably hexachloroacetone).

In another embodiment, the reaction is carried out in the absence of a halogenated organic solvent except perfluoromethylisopropyl ketone, perfluoromethylethyl ketone and a mixture thereof (preferably perfluoromethylisopropyl ketone).

In another embodiment, the reaction is carried out in the absence of a halogenated organic solvent except 2,2,2-trifluoroacetophenone, 2,2,2-trichloroacetophenone and a mixture thereof (preferably 2,2,2-trichloroacetophenone).

In another embodiment, the reaction is carried out in the absence of a halogenated organic solvent except hexachloroacetone, perfluoromethylisopropyl ketone, 2,2,2-trichloroacetophenone and any mixture thereof.

In another embodiment, terpinolene is reacted with an oxidizing agent comprising hydrogen peroxide in the presence of a halogenated ketone selected from halogenated di-($C_1$-$C_6$)-alkyl ketones and halogenated ($C_1$-$C_6$)-alkyl phenyl ketones (preferably from halogenated di-($C_1$-$C_4$)-alkyl ketones and halogenated ($C_1$-$C_4$)-alkyl phenyl ketones) as catalyst and the reaction is carried out in the absence of a halogenated organic solvent.

In another embodiment, terpinolene is reacted with an oxidizing agent comprising hydrogen peroxide in the presence of a halogenated ketone selected from halogenated di-($C_1$-$C_6$)-alkyl ketones (preferably from halogenated di-($C_1$-$C_4$)-alkyl ketones) as catalyst and the reaction is carried out in the absence of a halogenated organic solvent.

In another embodiment, terpinolene is reacted with an oxidizing agent comprising hydrogen peroxide in the presence of a halogenated ketone selected from hexafluoroacetone, hexachloroacetone, perfluoromethylisopropyl ketone, perfluoromethylethyl ketone, 2,2,2-trifluoroacetophenone, 2,2,2-trichloroacetophenone and any mixture thereof as catalyst and the reaction is carried out in the absence of a halogenated organic solvent.

In another embodiment, terpinolene is reacted with an oxidizing agent comprising hydrogen peroxide in the presence of a halogenated ketone selected from hexafluoroacetone, hexachloroacetone and a mixture thereof (preferably in the presence of hexachloroacetone) as catalyst and the reaction is carried out in the absence of a halogenated organic solvent.

In another embodiment, terpinolene is reacted with an oxidizing agent comprising hydrogen peroxide in the presence of a halogenated ketone selected from perfluoromethylisopropyl ketone, perfluoromethylethyl ketone and a mixture thereof (preferably in the presence of perfluoromethylisopropyl ketone) as catalyst and the reaction is carried out in the absence of a halogenated organic solvent.

In another embodiment, terpinolene is reacted with an oxidizing agent comprising hydrogen peroxide in the presence of a halogenated ketone selected from 2,2,2-trifluoroacetophenone, 2,2,2-trichloroacetophenone and a mixture thereof (preferably in the presence of 2,2,2-trichloroacetophenone) as catalyst and the reaction is carried out in the absence of a halogenated organic solvent.

In another embodiment, terpinolene is reacted with an oxidizing agent comprising hydrogen peroxide in the presence of a halogenated ketone selected from hexachloroacetone, perfluoromethylisopropyl ketone, 2,2,2-trichloroacetophenone and any mixture thereof as catalyst and the reaction is carried out in the absence of a halogenated organic solvent.

In another embodiment, terpinolene is reacted with an oxidizing agent comprising hydrogen peroxide in the presence of a catalytic amount of a halogenated ketone selected from halogenated di-($C_1$-$C_6$)-alkyl ketones and halogenated ($C_1$-$C_6$)-alkyl phenyl ketones (preferably from halogenated di-($C_1$-$C_4$)-alkyl ketones and halogenated ($C_1$-$C_4$)-alkyl phenyl ketones) and the reaction is carried out in the absence of a halogenated organic solvent.

In another embodiment, terpinolene is reacted with an oxidizing agent comprising hydrogen peroxide in the presence of a catalytic amount of a halogenated ketone selected from halogenated di-($C_1$-$C_6$)-alkyl ketones (preferably from halogenated di-($C_1$-$C_4$)-alkyl ketones) and the reaction is carried out in the absence of a halogenated organic solvent.

In another embodiment, terpinolene is reacted with an oxidizing agent comprising hydrogen peroxide in the presence of a catalytic amount of a halogenated ketone selected from hexafluoroacetone, hexachloroacetone, perfluoromethylisopropyl ketone, perfluoromethylethyl ketone, 2,2,2-trifluoroacetophenone, 2,2,2-trichloroacetophenone and any mixture thereof and the reaction is carried out in the absence of a halogenated organic solvent.

In another embodiment, terpinolene is reacted with an oxidizing agent comprising hydrogen peroxide in the presence of a catalytic amount of a halogenated ketone selected from hexafluoroacetone, hexachloroacetone and a mixture thereof (preferably in the presence of hexachloroacetone) and the reaction is carried out in the absence of a halogenated organic solvent.

In another embodiment, terpinolene is reacted with an oxidizing agent comprising hydrogen peroxide in the presence of a catalytic amount of a halogenated ketone selected from perfluoromethylisopropyl ketone, perfluoromethylethyl ketone and a mixture thereof (preferably in the presence of perfluoromethylisopropyl ketone) and the reaction is carried out in the absence of a halogenated organic solvent.

In another embodiment, terpinolene is reacted with an oxidizing agent comprising hydrogen peroxide in the presence of a catalytic amount of a halogenated ketone selected from 2,2,2-trifluoroacetophenone, 2,2,2-trichloroacetophenone and a mixture thereof (preferably in the presence of 2,2,2-trichloroacetophenone) and the reaction is carried out in the absence of a halogenated organic solvent.

In another embodiment, terpinolene is reacted with an oxidizing agent comprising hydrogen peroxide in the presence of a catalytic amount of a halogenated ketone selected from hexachloroacetone, perfluoromethylisopropyl ketone, 2,2,2-trichloroacetophenone and any mixture thereof and the reaction is carried out in the absence of a halogenated organic solvent.

In another embodiment, terpinolene is reacted with an oxidizing agent comprising hydrogen peroxide in the presence of a halogenated ketone selected from halogenated di-($C_1$-$C_6$)-alkyl ketones and halogenated ($C_1$-$C_6$)-alkyl phenyl ketones (preferably from halogenated di-($C_1$-$C_4$)-alkyl ketones and halogenated ($C_1$-$C_4$)-alkyl phenyl ketones) and the reaction is carried out in the absence of a halogenated organic solvent except halogenated di-($C_1$-$C_6$)-alkyl ketones and halogenated ($C_1$-$C_6$)-alkyl phenyl ketones (preferably halogenated di-($C_1$-$C_4$)-alkyl ketones and halogenated ($C_1$-$C_4$)-alkyl phenyl ketones).

In another embodiment, terpinolene is reacted with an oxidizing agent comprising hydrogen peroxide in the presence of a halogenated ketone selected from halogenated di-($C_1$-$C_6$)-alkyl ketones (preferably from halogenated di-($C_1$-$C_4$)-alkyl ketones) and the reaction is carried out in the absence of a halogenated organic solvent except halogenated di-($C_1$-$C_6$)-alkyl ketones (preferably halogenated di-($C_1$-$C_4$)-alkyl ketones).

In another embodiment, terpinolene is reacted with an oxidizing agent comprising hydrogen peroxide in the presence of a halogenated ketone selected from hexafluoroacetone, hexachloroacetone, perfluoromethylisopropyl ketone, perfluoromethylethyl ketone, 2,2,2-trifluoroacetophenone, 2,2,2-trichloroacetophenone and any mixture thereof and the reaction is carried out in the absence of a halogenated organic solvent except hexafluoroacetone, hexachloroacetone, perfluoromethylisopropyl ketone, perfluoromethylethyl ketone, 2,2,2-trifluoroacetophenone, 2,2,2-trichloroacetophenone and any mixture thereof.

In another embodiment, terpinolene is reacted with an oxidizing agent comprising hydrogen peroxide in the presence of a halogenated ketone selected from hexafluoroacetone, hexachloroacetone and a mixture thereof (preferably in the presence of hexachloroacetone) and the reaction is carried out in the absence of a halogenated organic solvent except hexafluoroacetone, hexachloroacetone and a mixture thereof (preferably hexachloroacetone).

In another embodiment, terpinolene is reacted with an oxidizing agent comprising hydrogen peroxide in the presence of a halogenated ketone selected from perfluoromethylisopropyl ketone, perfluoromethylethyl ketone and a mixture thereof (preferably in the presence of perfluoromethylisopropyl ketone) and the reaction is carried out in the absence of a halogenated organic solvent except perfluoromethylisopropyl ketone, perfluoromethylethyl ketone and a mixture thereof (preferably perfluoromethylisopropyl ketone).

In another embodiment, terpinolene is reacted with an oxidizing agent comprising hydrogen peroxide in the presence of a halogenated ketone selected from 2,2,2-trifluoroacetophenone, 2,2,2-trichloroacetophenone and a mixture thereof (preferably in the presence of 2,2,2-trichloroacetophenone) and the reaction is carried out in the absence of a halogenated organic solvent except 2,2,2-trifluoroacetophenone, 2,2,2-trichloroacetophenone and a mixture thereof (preferably 2,2,2-trichloroacetophenone).

In another embodiment, terpinolene is reacted with an oxidizing agent comprising hydrogen peroxide in the presence of a halogenated ketone selected from hexachloroacetone, perfluoromethylisopropyl ketone, 2,2,2-trichloroacetophenone and any mixture thereof and the reaction is carried out in the absence of a halogenated organic solvent except hexachloroacetone, perfluoromethylisopropyl ketone, 2,2,2-trichloroacetophenone and any mixture thereof.

In a preferred embodiment of the present invention, the reaction is carried out in a non-halogenated inert organic solvent. The solvent is preferably selected from non-halogenated aliphatic hydrocarbons, non-halogenated aromatic hydrocarbons and any mixtures thereof. Particular preference is given to non-halogenated aromatic hydrocarbons and any mixtures thereof.

Suitable non-halogenated aliphatic hydrocarbons contain 5 to 10 carbon atoms, for example, n-pentane, n-hexane, n-heptane, n-octane, n-nonane, n-decane and their isomers, petroleum ethers, cyclohexane, methylcyclohexane, any mixture thereof and the like.

Examples of suitable non-halogenated aromatic hydrocarbons are benzene, toluene, ethylbenzene, cymene, xylenes, mesitylene, any mixture thereof and the like. Preference is given to toluene and xylenes. Particular preference is given to toluene.

The volume ratio of the solvent to terpinolene is generally from 20:1 to 1:2, preferably from 8:1 to 1:2, more preferably from 6:1 to 1:2, most preferably from 4:1 to 1:2.

In another preferred embodiment of the present invention, the reaction is carried out without a solvent.

Alternatively, the epoxidation reaction may be carried out in a halogenated aromatic solvent. The halogenated aromatic solvent may be selected from halogenated aromatic hydrocarbons. Examples of suitable halogenated aromatic hydrocarbons are chlorobenzene, dichlorobenzene, any mixture thereof and the like. Preference is given to chlorobenzene. The aforementioned halogenated aromatic solvents are not part of this invention.

In a preferred embodiment of the present invention, the epoxidation reaction is carried out in the presence of an organic base.

The base is preferably selected from tertiary amines, pyridine, substituted pyridines, bicyclic amines and any mixture thereof. Preference is given to tertiary amines, pyridine, substituted pyridines and any mixture thereof. Particular preference is given to pyridine, substituted pyridines and any mixture thereof. Pyridine is especially preferred.

Examples of suitable tertiary amines are tri-($C_1$-$C_6$)-alkylamines such as trimethylamine, triethylamine, tributylamine and N,N-diisopropylethylamine; di-($C_1$-$C_6$)-alkyl-phenylamines such as N,N-dimethylaniline and N,N-diethylaniline; N-methyl imidazole, N,N-dimethylaminopyridine and the like.

Examples of suitable substituted pyridines are collidine, lutidines, picolines, N,N-dimethylaminopyridine and the like.

Examples of suitable bicyclic amines are 1,8-diazabicyclo[5.4.0]undec-7-en, 1,5-diazabicyclo-[4.3.0]non-5-ene, 1,4-diazabicyclo[2.2.2]octane and the like.

Preferably, the base of the present invention is selected from trimethylamine, triethylamine, tributylamine, N,N-diisopropylethylamine, N,N-dimethylaniline, N,N-diethylaniline, N-methyl imidazole, pyridine, collidine, lutidine, picoline, N,N-dimethylaminopyridine, 1,8-diazabicyclo-[5.4.0]undec-7-en, 1,5-diazabicyclo[4.3.0]non-5-ene, 1,4-diazabicyclo[2.2.2]octane and any mixture thereof.

More preferably, the base of the present invention is selected from trimethylamine, triethylamine, N,N-diisopropylethylamine, N,N-dimethylaniline, pyridine, collidine, lutidines, picolines, N,N-dimethylaminopyridine and any mixture thereof.

Most preferably, the base of the present invention is selected from pyridine, collidine, lutidines, picolines, N,N-dimethylaminopyridine and any mixture thereof.

Particularly preferred base is pyridine.

The molar ratio of the base to terpinolene can vary and is generally from 0.01:1 to 0.4:1, preferably from 0.02:1 to 0.3:1, more preferably from 0.02:1 to 0.25:1, most preferably from 0.02:1 to 0.2:1.

In a preferred embodiment of the present invention, terpinolene, halogenated ketone, and optionally the solvent are pre-charged in the reaction vessel and then the mixture is agitated, preferably under nitrogen atmosphere, before a premix of the base and hydrogen peroxide is added.

In another preferred embodiment of the present invention, terpinolene, the base and optionally the solvent are pre-charged in the reaction vessel and then the mixture is agitated, preferably under nitrogen atmosphere, before a premix of the halogenated ketone, and hydrogen peroxide is added.

In another preferred embodiment of the present invention, terpinolene, halogenated ketone, the base and optionally the solvent are pre-charged in the reaction vessel and then the mixture is agitated, preferably under nitrogen atmosphere, before hydrogen peroxide is added.

In another preferred embodiment of the present invention, terpinolene, halogenated ketone, and optionally the solvent are mixed together forming a first premix and the base, hydrogen peroxide and optionally a solvent are mixed together forming a second premix. The both premixes are then feeded to the reaction vessel, preferably under nitrogen atmosphere.

The process according to the present invention can be carried out under atmospheric pressure or under slightly elevated or reduced pressure. Typically, the atmospheric pressure is employed.

The epoxidation according to the present invention is usually effected at a room temperature, e.g. at 20 to 25° C. It can also be carried out at slightly elevated or reduced temperatures, e.g. at 5 to 40° C., preferably at 10 to 35° C. and more preferably at 15 to 30° C.

The pH of the reaction mixture can vary and is generally from 3 to 6, preferably from 4 to 5.

The molar ratio of the halogenated ketone to terpinolene can vary and is generally from 0.05:1 to 1:1, preferably from 0.05:1 to 0.8:1, more preferably from 0.05:1 to 0.5:1, even more preferably from 0.05:1 to 0.3:1, still more preferably from 0.05:1 to 0.2:1, yet more preferably from 0.075:1 to 0.2:1 and most preferably from 0.1:1 to 0.2:1. Excellent epoxidation yields can be obtained by using only a catalytic amount of the halogenated ketone as defined herein. Preferably, the process of this invention is carried out in the presence of a catalytic amount of the halogenated ketone as defined herein. By "catalytic amount" as used herein, it is meant that the molar amount of the halogenated ketone is relatively low in relation to the molar amount of terpinolene. For example, the catalytic amount of the halogenated ketone used in this invention is such that the molar ratio of the halogenated ketone to terpinolene is selected from any one of the aforementioned ratios.

The molar ratio of hydrogen peroxide to terpinolene can vary and is generally from 1:1 to 2:1, preferably from 1:1 to 1.8:1, more preferably from 1.1:1 to 1.7:1 and most preferably from 1.2:1 to 1.6:1.

Hydrogen peroxide is usually employed in form it aqueous solution, whereby the concentration of the solution is not critical. Usually the solution comprises 10% to 70% by weight, preferably 50 to 30% by weight of hydrogen peroxide.

The addition of hydrogen peroxide to the reaction mixture generally occurs in course of 0.1 to 7 hours, especially from 0.5 to 6 hours, more preferably from 1 to 5 hours.

Terpinolene epoxide of formula (I) can be further subjected to an epoxide ring opening isomerization leading to limonene-4-ol, optionally followed by conventional hydrogenation to give terpinene-4-ol, as described, for example in GB 1 307 053.

Terpinene-4-ol can in turn be used as a starting material for the synthesis of oxabicycloalkane herbicides, in particular of (±)-2-exo-(2-M ethyl benzyloxy)-1-methyl-4-isopropyl-7-oxabicyclo[2.2.1]heptane as described, for example in U.S. Pat. Nos. 4,487,945 or 4,542,244.

(±)-2-exo-(2-Methylbenzyloxy)-1-methyl-4-isopropyl-7-oxabicyclo[2.2.1]heptane (herein also referred to as the "exo-(±)-isomers", CAS RN 87818-31-3)

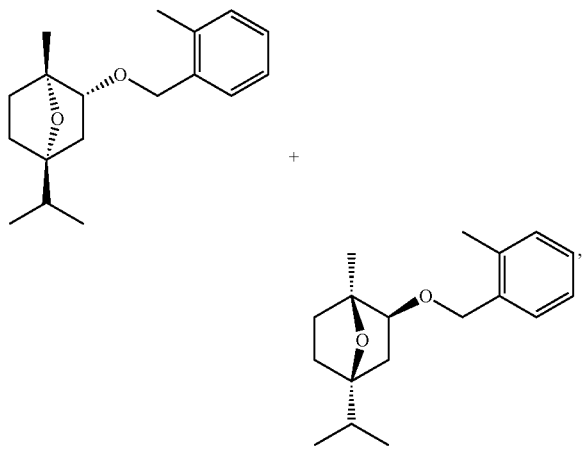

is the racemic mixture containing equal parts of the two enantiomers (+)-2-exo-(2-Methylbenzyloxy)-1-methyl-4-isopropyl-7-oxabicyclo[2.2.1]heptane (herein also referred to as the "exo-(+)-isomer", CAS RN 87818-61-9) and (−)-2-exo-(2-Methylbenzyloxy)-1-methyl-4-isopropyl-7-oxabicyclo[2.2.1]heptane (herein also referred to as the "exo-(−)-isomer", CAS RN 87819-60-1). The exo-(±)-isomers, the exo-(+)-isomer and the exo-(−)-isomer including their preparation and herbicidal properties are disclosed in EP 0 081 893 A2 (see Examples 29, 34, 35 and 62). Further preparation methods of these compounds are described in U.S. Pat. No. 4,487,945 (see Embodiments 46 and 48). The racemic mixture (±)-2-exo-(2-Methylbenzyloxy)-1-methyl-4-isopropyl-7-oxabicyclo[2.2.1]heptane is also described in the The Pesticide, Manual, Fourteenth Edition, Editor: C. D. S. Tomlin, British Crop Production Council, 2006, entry 157, pages 195-196 with its common name cinmethylin, its IUPAC name (1RS,2SR,4SR)-1,4-epoxy-p-menth-2-yl 2-methylbenzyl ether and its Chemical Abstracts name exo-(±)-1-methyl-4-(1-methylethyl)-2-[(2-methylphenyl) methoxy]-7-oxabicyclo[2.2.1]heptane.

Any of terpinolene epoxide of formula (I), limonene-4-ol and terpinene-4-ol are valuable intermediates in the preparation of (±)-2-exo-(2-Methylbenzyloxy)-1-methyl-4-isopropyl-7-oxabicyclo[2.2.1]heptane, any of its individual enantiomers or any non-racemic mixture thereof.

Any of terpinolene epoxide of formula (I), limonene-4-ol and terpinene-4-ol may be further converted into (±)-2-exo-(2-Methylbenzyloxy)-1-methyl-4-isopropyl-7-oxabicyclo [2.2.1]heptane, any of its individual enantiomers or any non-racemic mixture thereof. Further conversion into (±)-2-exo-(2-Methylbenzyloxy)-1-methyl-4-isopropyl-7-oxabicyclo[2.2.1]heptane, any of its individual enantiomers or any non-racemic mixture thereof can be accomplished by methods known in the art such as, for example, those described in EP 0 081 893 A2 and U.S. Pat. No. 4,487,945.

Thus, in a further aspect of the present invention, there is provided a process for preparing (±)-2-exo-(2-Methylbenzyloxy)-1-methyl-4-isopropyl-7-oxabicyclo[2.2.1]heptane, any of its individual enantiomers or any non-racemic mixture thereof comprising the steps of:
(i) preparing terpinolene epoxide of formula (I) (preferably limonene-4-ol, more preferably terpinene-4-ol) as described herein, and (ii) converting terpinolene epoxide of formula (I) (preferably limonene-4-ol, more preferably terpinene-4-ol) into (±)-2-exo-(2-Methylbenzyloxy)-1-methyl-4-isopropyl-7-oxabicyclo[2.2.1]heptane, any of its individual enantiomers or any non-racemic mixture thereof.

The invention is illustrated by the following examples without being limited thereto or thereby.

EXAMPLE 1: EPOXIDATION IN TOLUENE (0.10 EQ. HEXACHLOROACETONE)

400.0 g (90%; 2.64 mol) terpinolene, 70.0 g (0.26 mol) hexachloroacetone, 8.26 g (0.11 mol) pyridine and 700 g (2.88 mol) toluene were placed in a 2000 mL glass reactor and 287.6 g (50%; 1.6 mol) $H_2O_2$ was added within 5 h. The resulting mixture was stirred overnight at room temperature. Thereafter, aqueous $Na_2SO_3$-solution 1620 g (10%) was added. After stirring and phase split the solvent of the organic phase was evaporated. The distillation residue contained 58% of terpinolene epoxide, which corresponds to a yield of 81.5%.

EXAMPLE 2: EPOXIDATION IN TOLUENE (0.15 EQ. HEXACHLOROACETONE)

772.8 g (90.6%; 5.14 mol) terpinolene, 473.4 g (5.14 mol) toluene, 206.2 g (0.77 mol) hexachloroacetone and 16.4 g (0.21 mol) pyridine were placed in a 2500 mL glass reactor. 559.2 g (50%; 8.22 mol) $H_2O_2$ was dosed continuously over 2 h at 20-22° C. to the reaction mixture under vigorous stirring. The reaction mixture was stirred for further 6.5 h at 22° C.

Then phases were separated and water phase was collected in a bottle. To the organic phase in the reactor was added 474.9 g (0.57 mol) sodium sulfite solution (15% in water) in portions and the mixture was stirred for 30 minutes. Phases were separated. To the organic phase in the reactor was added 463 g sodium hydroxide solution (10% in water). After stirring and phase split the organic phase was washed three times with 342 g water in each case.

The solvent of the organic phase was distilled off at reduced pressure. The distillation residue (924 g) contained 68.2% of terpinolene epoxide (quantitative GC with internal standard), which corresponds to a yield of 80.5%.

The invention claimed is:
1. A process for the preparation of terpinolene epoxide of formula (I)

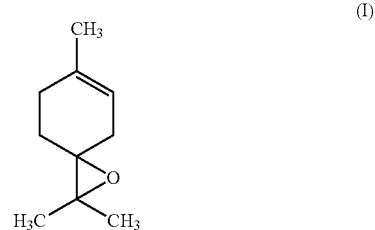

comprising reacting terpinolene with an oxidizing agent comprising hydrogen peroxide in the presence of a halogenated ketone selected from halogenated di-($C_1$-$C_6$)-alkyl ketones as catalyst and the reaction is carried out in a non-halogenated inert organic solvent and in the absence of a halogenated organic solvent except halogenated di-$(C_1$-$C_6)$-alkyl ketones.

2. The process according to claim 1, wherein the halogenated ketone is selected from hexafluoroacetone, hexachloroacetone, perfluoromethyl isopropyl ketone, perfluoromethyl ethyl ketone and any mixture thereof.

3. The process according to claim 1, wherein the halogenated ketone is hexachloroacetone.

4. The process according to claim 1, wherein the non-halogenated inert organic solvent is selected from non-halogenated aliphatic hydrocarbons, non-halogenated aromatic hydrocarbons and any mixture thereof.

5. The process according to claim 1, wherein the non-halogenated inert organic solvent is selected from non-halogenated aromatic hydrocarbons and any mixtures thereof.

6. The process according to claim 1, wherein the epoxidation is carried out in the presence of an organic base.

7. The process according to claim 6, wherein the base is selected from tertiary amines, pyridine, substituted pyridines, bicyclic amines and any mixture thereof.

8. The process according to claim 6, wherein the base is pyridine or substituted pyridines.

9. The process according to claim 6, wherein the pH of the reaction mixture is from 3 to 6.

10. The process according to claim 1, wherein the molar ratio of the halogenated ketone to terpinolene is from 0.05:1 to 1:1.

11. The process according to claim 1, wherein the molar ratio of hydrogen peroxide to terpinolene is from 1:1 to 2:1.

12. The process according to claim 1, wherein the epoxidation is carried out at 5 to 40° C.

13. The process according to claim 1, wherein the terpinolene epoxide of formula (I) is further subjected to an epoxide ring opening isomerization leading to limonene-4-ol.

14. The process according to claim 13, wherein limonene-4-ol is further reduced to give terpinene-4-ol.

15. A process for preparing (±)-2-exo-(2-Methylbenzyloxy)-1-methyl-4-isopropyl-7-oxabicyclo[2.2.1]heptane, any of its individual enantiomers or any non-racemic mixture thereof, comprising preparing the terpinolene epoxide of formula (I) in accordance with claim 1.

16. The process of claim 15, further comprising subjecting terpinolene epoxide of formula (I) to an epoxide ring opening isomerization to give limonene-4-ol.

17. The process of claim 16, further comprising hydrogenating limonene-4-ol to afford terpinene-4-ol.

18. The process of claim 17, further comprising treating terpinene-4-ol successively or concurrently with an oxidizing agent and an acid in an inert solvent to effect epoxidation and cyclization to give (±)-2-exo-hydroxy-1-methyl-4-isopropyl-7-oxabicyclo[2.2.1]heptane.

19. The process of claim 18, further comprising reacting (±)-2-exo-hydroxy-1-methyl-4-isopropyl-7-oxabicyclo[2.2.1]heptane with a compound of the formula $WCH_2L$ wherein W is 2-methylphenyl and L is a leaving group to afford (±)-2-exo-(2-Methylbenzyloxy)-1-methyl-4-isopropyl-7-oxabicyclo[2.2.1]heptane, any of its individual enantiomers or any non-racemic mixture thereof.

* * * * *